United States Patent
Breininger et al.

(10) Patent No.: US 10,929,975 B2
(45) Date of Patent: Feb. 23, 2021

(54) CHECKING AN INTERVENTIONAL SUPERPOSITION IMAGE

(71) Applicant: Siemens Healthcare GmbH, Erlangen (DE)

(72) Inventors: Katharina Breininger, Erlangen (DE); Marcus Pfister, Bubenreuth (DE); Markus Kowarschik, Nuremberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 84 days.

(21) Appl. No.: 16/404,008

(22) Filed: May 6, 2019

(65) Prior Publication Data

US 2019/0347793 A1 Nov. 14, 2019

(30) Foreign Application Priority Data

May 9, 2018 (EP) ..................................... 18171646

(51) Int. Cl.
 *G06T 7/00* (2017.01)
 *G06K 9/46* (2006.01)
 *G06N 3/08* (2006.01)

(52) U.S. Cl.
 CPC .......... *G06T 7/0012* (2013.01); *G06K 9/4609* (2013.01); *G06N 3/08* (2013.01); *G06T 2207/10121* (2013.01)

(58) Field of Classification Search
 CPC ......... G06T 7/0012; G06T 2207/10121; G06T 7/0014; G06T 7/337; G06T 2207/30101;
 (Continued)

(56) References Cited

U.S. PATENT DOCUMENTS

| | | | |
|---|---|---|---|
| 7,822,241 B2 * | 10/2010 | Eck | A61B 6/504 382/128 |
| 2011/0235876 A1 | 9/2011 | Pfister et al. | |
| 2019/0347793 A1 * | 11/2019 | Breininger | G06T 7/0012 |

FOREIGN PATENT DOCUMENTS

DE 102010012621 A1 9/2011

OTHER PUBLICATIONS

Pierre Ambrosini et al: "Fully Automatic and Real-Time Catheter Segmentation in X-Ray Fluoroscopy"; arxiv.org, Cornell University Library, 201 Olin Library Cornell University Ithaca, NY 14853, Jul. 17, 2017 (Jul. 17, 2017), XP080777275; DOI: 10.1007/978-3-319-66185-8 65; 2017.

(Continued)

*Primary Examiner* — Diane D Mizrahi
(74) *Attorney, Agent, or Firm* — Harness, Dickey & Pierce, P.L.C

(57) ABSTRACT

A method and computing unit are for automatically checking a superposition image of a body region of interest of an examination object. The method and computing unit include determining at least one reference position of an object in a reference image; determining a current position of the object; generating the superposition image by superimposing the current fluoroscopic image and the reference image; determining at least one parameter characterizing a measure of discrepancy; and displaying the measure of discrepancy determined. Further, in at least one embodiment, the various aspects of the method or performed by at least one processor of the computing unit, are performed in quasi real time.

20 Claims, 5 Drawing Sheets

(58) Field of Classification Search
CPC .... G06T 2207/30004; G06T 2207/30008; G06K 9/4609; G06N 3/08; G16H 30/40; A61B 6/504; A61B 6/4441
See application file for complete search history.

(56) References Cited

OTHER PUBLICATIONS

Breininger Katharina et al: "Intraoperative stent segmentation in X-ray fluoroscopy for endovascular aortic repair"; International Journal of Computer Assisted Radiology and Surgery, Springer, DE, Bd. 13, Nr. 8, 19. Mai 2018 (May 19, 2018); pp. 1221-1231, XP036559998, ISSN: 1861-6410, DOI: 10.1007/S11548-018-1779-6; 2018.

Lessard, Simon et al. "Automatic detection of selective arterial devices for advanced visualization during abdominal aortic aneurysm endovascular repair" Medical Engineering and Physics, vol. 37 No. 10, pp. 979-986, 2015 http://dx.doi.org/10.1016/j.medengphy.2015.07.007.

Kauffmann, Claude et al. "Source of Errors and Accuracy of a TwoDimensional/Three-Dimensional Fusion Road Map for Endovascular Aneurysm Repair of Abdominal Aortic Aneurysm" Journal of Vascular and Interventional Radiology, vol. 26, No. 4, pp. 544-551, Apr. 2015 // DOI: https://doi.org/10.1016/j.jvir.2014.12.019.

Toth, Daniel et al. "Adaption of 3D Models to 2D X-Ray Images during Endovascular Abdominal Aneurysm Repair" MICCAI 2015: Medical Image Computing and Computer-Assisted Intervention, vol. 9349, Springer, Cham, pp. 339-346, 2015; DOI: https://doi.org/10.1007/978-3-319-24553-9_42 Online ISBN: 978-3-319-24553-9.

Virga Salvatore et al.: "Optimal C-arm Positioning for Aortic Interventions" In: "Informatik Aktuell."; Feb. 25, 2015 (Feb. 25, 2015), Springer Verlag, London., GB, XP055515291; ISSN: 1431-472X; pp. 53-58, DOI: 10.1007/978-3-662-46224-9 11; 2015.

European Search report for European Patent Application No. 18171646, dated Oct. 18, 2018.

* cited by examiner

CHECKING AN INTERVENTIONAL SUPERPOSITION IMAGE

PRIORITY STATEMENT

The present application hereby claims priority under 35 U.S.C. § 119 to European patent application number EP 18171646.5 filed May 9, 2018, the entire contents of which are hereby incorporated herein by reference.

FIELD

Embodiments of the invention generally relate to devices/methods for checking an interventional superposition image and in particular, to a method for the automatic evaluation of superposition image quality in real time.

BACKGROUND

Fluoroscopy-guided interventions are typically performed on angiographic systems or mobile C-arm systems, which each use X-ray imaging. Fluoroscopy is used when "real-time examination" of a patient is required. Typical applications of fluoroscopy include functional tests on orthopedic joint replacements, controlling catheters and cardiac pacemakers, distribution of contrast medium in the gastrointestinal tract, movement of various body parts and organs (for example swallowing and movement of the esophagus) or minimally invasive surgery to repair aneurysms, for example in the abdominal aorta.

An abdominal aortic aneurysm (AAA) is a bulging of the vessel. This is treated, for example, by the insertion of a stent graft. For this purpose, guidewires and catheters are introduced into the aorta via both groins, via which one or more stent grafts, i.e. plastic vessels or endoprostheses, are introduced and positioned. In the case of complex interventions, not only the aorta, but also the various branches, such as, for example, renal arteries are provided with special stents. The final stent is therefore composed of a plurality of different individually introduced 'partial stents'.

The objective of the insertion of these stent grafts is to position them precisely without thereby covering important branch-off vessels. To visualize the vessels, two-dimensional fluoroscopic images are recorded continuously throughout the entire intervention by way of a C-arm X-ray system in order to monitor and control the feed rate, position and/or location of catheters, guidewires, endoprostheses and/or blood vessels.

Angiograms (typically two-dimensional projections with contrast medium administration) can also be produced on C-arm systems that provide information on the course of a blood vessel. Advantageously, these angiograms can be superimposed on the current fluoroscopic images as so-called 'roadmaps'. However, in order to minimize the administration of nephrotoxic contrast media, information from reference images (usually preoperative, three-dimensional computed-tomography or MRI images) can be superimposed in an anatomically correct manner on a current fluoroscopic image.

The reference images typically show additional anatomical details or reference points, such as, for example, vascular branches or depth information that is not resolved in fluoroscopy, which are used as positioning aids for the medical material to be introduced. Three-dimensional datasets can, in principle, also be superimposed on every fluoroscopic image independently of the angulation set on the C-arm, i.e. independently of the viewing direction of the region of interest of the patient's body adopted for the imaging.

Segmentation of anatomical objects and/or further structures by way of known segmentation methods is expediently used to obtain the superimposition of fluoroscopic images and reference image data. A prerequisite for the superimposition is the registration of the preoperative reference images to the C-arm by way of known registration methods in order to achieve conformity between the reference image and the current image.

In addition, methods are known for identifying and tracking medical instruments or material in the fluoroscopic images, such as, for example, those described in LESSARD, S. et. al.: "Automatic detection of selective arterial devices for advanced visualization during abdominal aortic aneurysm endovascular repair", in: Med Eng Phys., 2015, Vol. 37(10), pp. 979-986 for the described application of an aortic aneurysm.

However, particularly with complex procedures, the accuracy or the quality of the superimposition, i.e. the conformity between two-dimensional fluoroscopic images and the reference image data, is impaired. The reason for this may be, on the one hand, patient movement, since in particular minimally invasive interventions are frequently performed with local anesthesia only. On the other, the surgical instruments introduced regularly cause deformation of the anatomy. The greater the discrepancies between the current image and the reference data, the less useful the display of the superimposition to the viewer. During the intervention, the viewer has to identify the discrepancy visually and correct it 'mentally'. Alternatively, to this end, the superimposition can also be corrected manually or automatically on user initiation or semi-automatically by individual viewer specifications, such as is described, for example, in the German patent application DE 102010012621 A1 or in TOTH et al., "Adaption of 3D Models to 2D X-Ray Images during Endovascular Abdominal Aneurysm Repair", In: Navab N., Hornegger J., Wells W., Frangi A. (eds) Medical Image Computing and Computer-Assisted Intervention—MICCAI 2015. Lecture Notes in Computer Science, vol 9349, Springer, Cham.

SUMMARY

The inventors have discovered that this procedure at least requires the discrepancy to be identified by the user, interrupts the work of surgical personnel and is also time-consuming and, in particular for untrained viewers, difficult and hence error-prone.

In contrast, embodiments of the present invention provides alternative ways that enable the quality of a superposition image with respect to anatomical discrepancies to be ascertained automatically, reliably and quickly. It is in particular, embodiments of the present invention ascertain the quality of the superposition image in real time or quasi real-time.

Embodiments of the invention are directed to a method for automatically checking a superposition image of a body region of interest of an examination object, a corresponding computing unit and medical imaging system, a corresponding computer program and a corresponding computer-readable data carrier. Preferred and/or alternative, advantageous variants are the subject matter of the claims.

The following describes the achievement of embodiments according to the invention in relation to the claimed method and in relation to the claimed devices. Features, advantages or alternative embodiments mentioned herein can similarly be transferred to the other claimed subject matter and vice versa. In other words, the substantive claims (which are, for example, directed at a method) can also be developed with the features described or claimed in conjunction with one of the devices. Herein, the corresponding functional features of the method are formed by appropriate substantive modules or units.

The present invention relates in a first embodiment to a method for automatically checking a superposition image of a body region of interest of an examination object.

In an embodiment, the method includes:
determining at least one reference position of an object in a reference image;
determining a current position of the object in a current fluoroscopic image;
generating the superposition image by superimposing the current fluoroscopic image and the reference image;
determining at least one parameter characterizing a measure of discrepancy between the at least one reference position of an object and the current position of the object in the superposition image; and
displaying the measure of discrepancy determined.

In a second embodiment, the present invention relates to a computing unit for automatically checking a superposition image of a body region of interest of an examination object.

The computing unit of the second embodiment comprises at least one processor, configured to:
determine at least one reference position of an object in a reference image;
determine a current position of the object in a current fluoroscopic image;
generate the superposition image by superimposing the current fluoroscopic image and the reference image;
determine at least one parameter characterizing a measure of discrepancy between the at least one reference position of an object and the current position of the object in the superposition image; and
display the measure of discrepancy determined.

In a third embodiment, the invention relates to a medical imaging system in the form of a C-arm X-ray device. The medical imaging system advantageously includes a computing unit according to at least one embodiment of the invention. A medical imaging system is an imaging system for use in medicine. A medical imaging system according to at least one embodiment of the invention uses X-rays for the generation of images. The medical imaging system is preferably suitable for use in medical interventions, i.e. for real time-imaging. The medical imaging system can in particular be designed as a mobile C-arm X-ray system.

A fourth embodiment of the present invention relates to a computer program with program code for carrying out the method according to at least one embodiment of the invention for automatically checking a superposition image of a body region of interest of an examination object when the computer program is executed on a computer, for example the computing unit according to at least one embodiment of the invention.

A fifth embodiment of the present invention relates to a computer-readable data carrier with program code of a computer program for carrying out the method according to at least one embodiment of the invention for automatically checking a superposition image of a body region of interest of an examination object when the computer program is executed on a computer, for example the computing unit according to at least one embodiment of the invention. Advantageously, it is possible to perform in particular the step of the determination of at least one parameter characterizing a measure of discrepancy between the reference position and the current position of the object in a superposition image on a computer, for example in a computing unit of a medical imaging system.

BRIEF DESCRIPTION OF THE DRAWINGS

The above-described properties, features and advantages of embodiments of the invention and the manner in which these are achieved will become clearer and more plainly comprehensible in conjunction with the following description of the example embodiments explained in more detail in conjunction with the drawing. This description does not restrict the invention to these example embodiments. In the different figures, the same components are given identical reference characters. The figures are generally not true to scale. The figures show.

DETAILED DESCRIPTION OF THE EXAMPLE EMBODIMENTS

Figure 1:
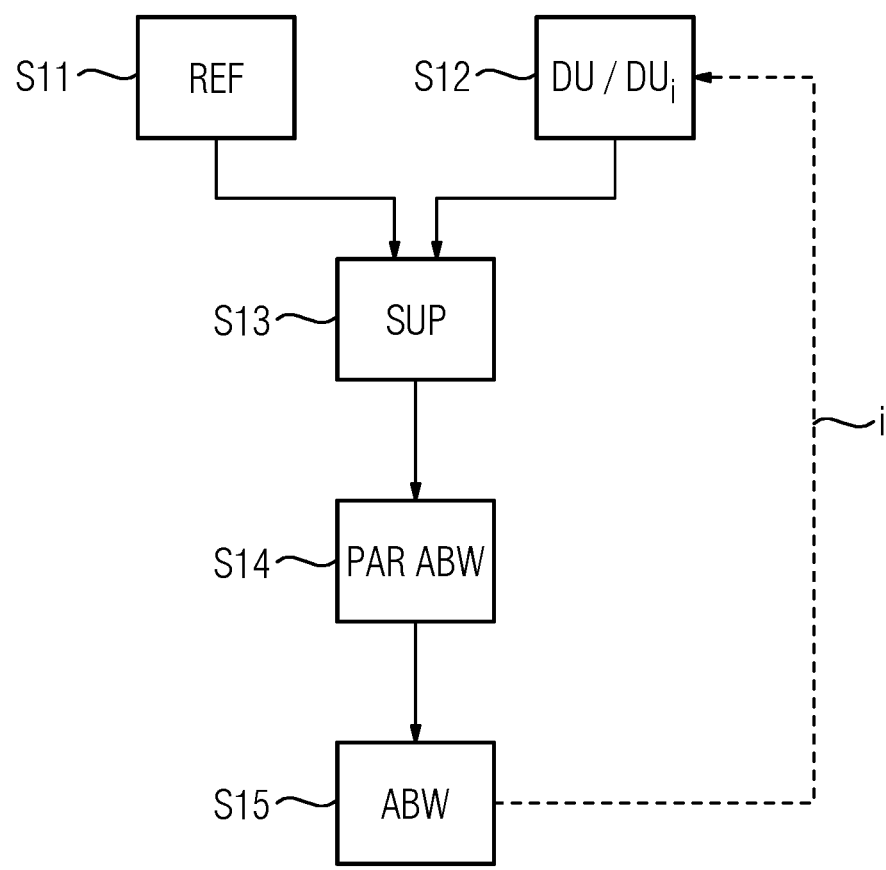
FIG. 1 a schematic representation of a method according to the invention according to an example embodiment of the present invention, FIG. 2 a schematic representation of a method according to the invention according to another example embodiment of the present invention, FIG. 3 a schematic representation of a method according to the invention according to a further example embodiment of the present invention, FIG. 4 a view of a medical imaging system in the form of a C-arm X-ray device according to an embodiment of the present invention comprising a computing unit according to the invention according to an example embodiment of the present invention, FIG. 5 a superposition image according to an example embodiment of the present invention, and FIG. 6 a superposition image according to an example embodiment of the present invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but they may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

The present invention relates in a first embodiment to a method for automatically checking a superposition image of a body region of interest of an examination object.

Hereinafter, it is assumed, without restricting generality, that the examination object is a patient, wherein this is generally a person. In principle, the patient can also be an animal. Therefore, hereinafter, the two terms "examination object" and "patient" are used synonymously. Alternatively, the examination object can be a plant or a non-living object, for example a historical artifact or the like. The body region of interest describes a region, partial region and/or body part of the patient that includes certain anatomical structures, organs and/or tissues that are to be depicted via a medical imaging system. For example, the body region of interest can be the abdomen, the head and/or the thorax. The superposition image depicting the body region of interest can, for example, depict the course of blood vessels within the body region of interest. Alternatively, the superposition image can also depict bony structures, such as the skull, hip or spine. However, the superposition image is not restricted thereto, it can substantially depict all anatomical objects or structures that can be imaged using a reference image and/or fluoroscopic image (generally generated with the use of contrast media).

The method of at least one embodiment includes a plurality of steps. A first step entails the determination of a reference position of at least one object in a reference image.

A second step entails the determination of a current position of the object in a current fluoroscopic image. According to the invention, the current fluoroscopic image corresponds to a current fluoroscopic image acquired at a point in time during the course of an intervention, i.e. a medical intervention. The current fluoroscopic image is preferably a two-dimensional projection acquired via a C-arm X-ray system, but it can also correspond to a three-dimensional dataset. The fluoroscopic image is typically acquired without the administration of contrast medium, but can also be generated with the administration of contrast medium.

According to at least one embodiment of the invention, the reference image corresponds to a preferably three-dimensional image dataset. This was acquired or generated at a reference time point, preferably before the medical intervention. The reference image is, for example, embodied as a computed-tomography image or magnetic-resonance image. The reference image can also be embodied as a two-dimensional image. Common to the current fluoroscopic image and the reference image is that fact that they both depict the same body region of interest of the patient and hence directly or indirectly include the same anatomical objects or structures within the body region of interest.

In particular, the images can each depict blood vessels, i.e. at least one and the same blood vessel. The body region of interest depicted preferably includes a plurality of blood vessels or a vessel and branch-off vessels, ramifications and/or an entire vascular tree. The determination of a reference position of at least one object in the reference image is performed for at least one depicted object manually and/or by way of a segmentation method that is known per se. The at least one object can in particular be a blood vessel, but it can also be a specific bone or tissue structure, a specific organ or the like. If the object is a blood vessel, the determination of the position in the reference image and/or current fluoroscopic image can include the determination of the course of the blood vessel. The segmentation can in particular include the determination of outer contours of the blood vessels, approximated circumferences, centerlines of the blood vessels, specific landmarks such as, for example, branch-off vessels and/or branches, diameters of the blood vessels or the like.

In a preferred embodiment of the method according to the invention, in which the object is a blood vessel, the determination of the current position of the object in the current fluoroscopic image includes the identification or segmentation of an instrument located in the blood vessel, an endo-prosthesis such as, for example, a stent or stent part, an aortic valve or cardiac valve, the outer contour and/or the volume of the blood vessel. Herein, the invention is based on the assumption that the position or location of medical instruments, insofar as they are within the blood vessel, substantially represent the current position or the current course of the blood vessel.

A further step entails the generation of the superposition image by superimposing the current fluoroscopic image and the reference image. To this end, generally at the start of the medical intervention, the reference image is registered to existing fluorescent images, i.e. brought into conformity based on various common features (for example the course of vessels or bone structure). Preferably, the conformity is good enough to be valid for other viewing directions as well. Methods that are known per se can be used for the registration.

A further step entails the determination of at least one parameter characterizing a measure of discrepancy between the reference position and the current position of an object in the superposition image. The superimposition of the reference image and the current fluoroscopic image can, for example, reveal differences between the current course and the reference course due to patient movement and/or for the preferred case "object=blood vessel" due to the medical instruments introduced into the blood vessel. The current position can be displaced, twisted, stretched and/or the like relative to the reference position. These discrepancies are visualized by the superposition and automatically quantized in the current step.

Insofar, the parameter determined indicates the quality of the superimposition in the superposition image. For example, in the case "object=blood vessel", it can indicate a surface portion of a stent in the current fluoroscopic image, which, in the superposition image, is outside the blood vessel according to the reference course. The parameter can indicate a distance between the outer vascular contours in the reference image and the current fluoroscopic image. The parameter can also indicate whether a medical instrument representing the current position or the current course of a blood vessel is inside or outside the blood vessel according to the reference position or course. Herein, a plurality of other parameters is conceivable in order to quantify the discrepancies. According to the invention, at least one parameter, but preferably a plurality of different parameters, is calculated.

A further step entails displaying the measure of discrepancy for a user. The superposition image is typically displayed to a surgeon or surgical personnel during the course of a medical intervention as visual support, for example on a monitor of a C-arm X-ray system. The inventors have now recognized that it is particularly advantageous, in addition to the superposition image per se, for the surgical personnel also to be shown the calculated degree of discrepancy between the current fluoroscopic image and reference image. This enables account to be taken of the quality of the superposition. Particularly preferably, the measure of discrepancy is visualized together with or in the superposition.

Other display modes or output modes are also conceivable. A visual display can, for example take the form of the display of the determined value for at least one parameter. Alternatively, it is possible, in dependence on at least one parameter, for a colored signal lamp corresponding to its determined value to be inserted, for example 'green' for no discrepancies or small discrepancies only, and 'red' for larger or critical discrepancies. In order to further illustrate the measure of discrepancy, segmented structures can be marked in color in the superposition image according to the reference position and the current position of the object, for example vessel and/or stent outer contours.

In an advantageous embodiment of the method according to the invention, the steps
  determination of a current position of the object in the current fluoroscopic image,
  generation of the superposition image by superimposing the current fluoroscopic image and the reference image,
  determination of at least one parameter characterizing a measure of discrepancy between the reference position and the current position of the object in the superposition image, and
  displaying the measure of discrepancy for a user are performed in quasi real time.

As a result, there are no delays that could be disruptive or critical to the patient's health during the course of the medical intervention. Herein, quasi real time describes a maximum time that elapses until the display of the superposition together with the measure of discrepancy. According to the invention, this time is shorter than the time between the acquisition of two fluorescent images during the course of the medical intervention.

In a particularly preferred embodiment of the method according to the invention, the segmentation, in particular of the current fluoroscopic image, is performed using a neural network or by way of a template-matching technique. The time-limiting step in the method according to the invention is the identification, i.e. the segmentation of the depicted structures or objects, in particular the blood vessels. The inventors have now recognized that the use of the techniques named enables the process to be accelerated to quasi real time. The choice of a suitable segmentation method depends on the individual application or the body region of interest.

So-called template matching is commonly used for the identification of objects in images and utilizes information on the structure, shape, orientation and/or color of the objects. The described properties are specified by a pattern and an image matching this pattern is sought. If an object identified in the image achieves a predetermined a degree of conformity, it is selected as the sought object.

A neural network, in particular an artificial neural network is based on the structure of a biological neural network such as, for example, a human brain. An artificial neural network has an input layer and an output layer preferably with a plurality of further layers sandwiched therebetween, each of which has at least one node. Herein, each node corresponds to a processing unit, similarly to a biological neuron. Nodes within a layer of the network can be connected via directional links (edges) to nodes in other layers. The links define the data flow within the network. Consequently, each node represents an operation that is applied to the input data. Furthermore, each node or each of its links has a weighting parameter. This weighting parameter defines the influence or importance of the output from a node as the input value for a receiving node. In the training phase, which is preferably performed as monitored learning, the artificial neural network uses training data to 'learn' the weighting parameters for all the nodes or links and adapts these until the output layer of the network supplies the correct output values. Typically, a first part of network layers is used for feature extraction in images. The identified features are then used as input values for a second part of network layers, the so-called classifiers, which assign objects present in the images to the extracted features.

In a further embodiment of the method according to the invention, the steps
  determination of a current position of the object in the current fluoroscopic image,
  generation of the superposition image by superimposing the current fluoroscopic image and the reference image,
  determination of at least one parameter characterizing a measure of discrepancy between the reference position and the current position of the object in the superposition image, and
  displaying the measure of discrepancy for a user. are performed continuously for a plurality of successive fluorescent images.

This procedure is based on the knowledge that patient movements and/or the continuous shifting, displacement or introduction of further medical instruments or materials into a blood vessel during a medical intervention causes the current position of the at least one object to change continuously relative to the reference position. The continuous repetition of the method according to the invention provides a permanent control option. In this sense, the present invention is suitable for a plurality of medical interventions, such as, for example, the use of stents (intracranial, abdominal, thoracic, coronary) or cardiac or aortic valves or robot-assisted interventions.

In a further embodiment of the method according to the invention, the determination of the parameter characterizing the measure of discrepancy takes account of previous knowledge of segmented structures from at least one previously analyzed fluoroscopic image. This procedure makes use of the knowledge that structures are already known for a previous, not necessarily directly preceding, fluoroscopic image and parameters characterizing the measure of discrepancy have been determined or calculated. These can be used in the sense of a plausibility check during the evaluation of the current fluoroscopic image or the associated superposition image, for example in that it is automatically checked whether a previously and currently determined parameter characterizing the measure of discrepancy is within (result is plausible) or outside (result is not plausible) a predetermined range of values. Herein, it is assumed that changes to the current position, in particular to the current course of a blood vessel, between fluorescent images that are adjacent or close in time to one another are small.

Another embodiment of the method according to the invention includes the following steps:
automatic generation of a corrected superposition image based on the parameter characterizing the measure of discrepancy between the reference position and the current position of the object
determination of at least one parameter characterizing a corrected measure of discrepancy between the reference position and the current position of the object in the corrected superposition image and
displaying the corrected measure of discrepancy for a user.

If the determined, at least one, parameter characterizing the measure of discrepancy is above a predetermined tolerance or a predetermined threshold value, this indicates that the superimposition between the current fluoroscopic image and the reference image is not of sufficient quality and needs to be corrected. A corrected superposition image can be generated using the teaching cited in the introduction from the German patent application DE 102010012621 A1 or TOTH et al., "Adaption of 3D Models to 2D X-Ray Images during Endovascular Abdominal Aneurysm Repair", in: Navab N., Hornegger J., Wells W., Frangi A. (eds) Medical Image Computing and Computer-Assisted Intervention—MICCAI 2015, the entire contents of each of which are hereby incorporated herein by reference. Lecture Notes in Computer Science, vol 9349, Springer, Cham, the entire contents of which are hereby incorporated herein by reference.

The correction of the superimposition improves the quality of the superimposition of the structures in the corrected superposition image. The correction is substantially based on the adaptation of the reference position of an object and in particular of the reference course of a blood vessel to the current position or the current course of the current fluorescent image. The corrected superposition image provides surgical personnel with an enhanced degree of clinical information. The correction can, for example, be performed automatically in dependence on the determined parameter characterizing the measure of discrepancy or automatically suggested to the user for confirmation. Alternatively, surgical personnel can trigger the correction manually. The corrected superposition image is then evaluated in the further course of the method according to the invention and a parameter for a corrected measure of discrepancy determined. The described procedure can be designed iteratively and continued until the at least one parameter characterizing a measure of discrepancy falls below a predetermined threshold value. In particular, the procedure described here can be combined with the following embodiment and applied to a modified superposition image.

A further preferred embodiment of the method according to the invention also includes the following steps:
based on the parameter characterizing the measure of discrepancy, derivation of at least one acquisition parameter for a medical imaging system if the parameter for the measure of discrepancy exceeds a predetermined threshold value
acquisition of a modified fluoroscopic image using the acquisition parameter
determination of a current position of the object in the modified fluoroscopic image
generation of a modified superposition image by superimposing the modified fluoroscopic image and the reference image
determination of at least one parameter characterizing a modified measure of discrepancy between the reference position and the current position of the object in the superposition image
displaying the modified measure of discrepancy for a user.

If at least one of the determined parameters characterizing a measure of discrepancy has a value outside a predetermined range of values or above a predetermined threshold value, this indicates that the discrepancies in the location, position or course of the segmented structures in the current fluoroscopic image and reference image are so great that it is not possible to achieve a meaningful superimposition in the sense that the superimposition cannot be corrected in the way described above.

In this situation, at least one embodiment of the invention suggests in dependence on the parameter characterizing the measure of discrepancy the derivation of at least one acquisition parameter for the acquisition of a new, modified fluoroscopic image. Insofar, the method according to the invention can suggest at least one acquisition parameter, for example changed angulation, changed collimation, changed X-ray tube voltage or the like, and acquire a modified fluoroscopic image, which is more suitable for correction as described above. The derivation of an acquisition parameter can be user-triggered or take place automatically. The acquisition of the modified fluoroscopic image with the derived acquisition parameter can be user-triggered.

The method according to at least one embodiment of the invention is then performed using the modified fluoroscopic image and a parameter characterizing a modified measure of discrepancy determined. If, after the performance of the described steps, the parameter characterizing the measure of discrepancy is still not within the tolerance, the method can be repeated, another acquisition parameter derived and a modified fluoroscopic image acquired etc.

Therefore, in this embodiment, a serious 'mismatch' between the reference image and the current fluoroscopic image is identified. This can be due to too small an image field, a lack of structural information on the body region of interest and/or unfavorable angulation/collimation of the current fluoroscopic image. As a result, at least one acquisition parameter is suggested for acquiring a further fluoroscopic image, which will probably allow a correction.

In a second embodiment, the present invention relates to a computing unit for automatically checking a superposition image of a body region of interest of an examination object.

The computing unit comprises devices for carrying out the method according to at least one embodiment of the invention.

In a preferred embodiment, the computing unit is connected to a medical imaging system such that control signals relating to corrected acquisition parameters or current and/or modified fluorescent images can be transmitted. Also advantageously, the computing unit is connected to a display unit of a medical imaging system for displaying a (corrected/modified) superposition image and/or a (corrected/modified) measure of discrepancy.

The computing unit is advantageously integrated in the medical imaging system. Alternatively, the computing unit can also be remote or separate therefrom. The computing unit can be designed to perform in particular the step of the determination of at least one parameter characterizing a measure of discrepancy between the reference position and the current position of the object in a superposition image, but also the entire method according to the invention, for one medical imaging system or for a plurality of systems, for example in a radiology center or hospital with multiple medical imaging systems.

In a third embodiment, the invention relates to a medical imaging system in the form of a C-arm X-ray device. The medical imaging system advantageously includes a computing unit according to at least one embodiment of the invention. A medical imaging system is an imaging system for use in medicine. A medical imaging system according to at least one embodiment of the invention uses X-rays for the generation of images. The medical imaging system is preferably suitable for use in medical interventions, i.e. for real time-imaging. The medical imaging system can in particular be designed as a mobile C-arm X-ray system.

A fourth embodiment of the present invention relates to a computer program with program code for carrying out the method according to at least one embodiment of the invention for automatically checking a superposition image of a body region of interest of an examination object when the computer program is executed on a computer, for example the computing unit according to at least one embodiment of the invention.

A fifth embodiment of the present invention relates to a computer-readable data carrier with program code of a computer program for carrying out the method according to at least one embodiment of the invention for automatically checking a superposition image of a body region of interest of an examination object when the computer program is executed on a computer, for example the computing unit according to at least one embodiment of the invention. Advantageously, it is possible to perform in particular the step of the determination of at least one parameter characterizing a measure of discrepancy between the reference position and the current position of the object in a superposition image on a computer, for example in a computing unit of a medical imaging system.

The embodiment of the invention in the form of a computer program or a computer-readable carrier with program code of a computer program according to at least one embodiment of the invention has the advantage that existing computer systems or computing units can be easily adapted by a software update in order to achieve a function according to at least one embodiment of the invention.

The computer program can alternatively be embodied in the form of a computer program product and comprise additional units. These can be embodied in the form of hardware, for example as a storage medium on which the computer program is stored and/or a hardware key to enable use of the computer program. Alternatively or additionally, it can be in the form of software, for example program documentation or a software key to enable the computer program to be used.

FIG. 1 is a schematic representation of a method according to the invention with a plurality of steps according to an example embodiment of the present invention. A first step S11 entails the determination of a reference position of an object in the form of a reference course of at least one blood vessel in a reference image REF. Here, the determination is performed by way of segmentation but can also performed in another way. In other words, the reference image is 'searched' for anatomical structures.

To be specific, it is possible to acquire outer contours or outer surfaces of a blood vessel, vessel valves, branch vessels, vessel volumes, vessel diameters, vessel centerlines, significant distances to other depicted structures or organs, the actual organs or structures or the like by way of segmentation methods. At least one depicted blood vessel, for example the abdominal aorta, is analyzed in this way. The reference image can be a three-dimensional CT, MR or C-arm image dataset (for example a rotational angiogram) or a two-dimensional image dataset (for example a digital subtraction angiogram acquired via a C-arm X-ray device).

Step S11 is preferably performed at a separate time from the other steps S12 to S15. For example, if the reference image has already been preprocessed, it is advantageously possible to save on computing time and computing capacity during the course of a medical intervention. A second step S12 entails a determination of a current position of the object in the form of a current course of the blood vessel using a current fluoroscopic image DU. This is acquired during the course of a medical intervention by way of a medical imaging system in the form of a C-arm X-ray device as a digital X-ray projection with a specific angulation of the C-arm system. The fluoroscopic image corresponds to a snapshot of the depicted body region of interest of the patient and also shows in particular medical equipment, endoprostheses, instruments and the like located in the body region of interest and in particular in the blood vessel.

Step S12 entails a segmentation of these objects in the current fluoroscopic image DU. The current course of the blood vessel is determined under the assumption that the segmented objects are located within the blood vessel; insofar the current course of the blood vessel is approximated by the position, location, extension, elongation or the like of these objects. If the current fluoroscopic image DU was generated with the administration of contrast medium (and a sufficient contrast between the blood vessels and the surrounding tissue is achieved), the determination can also include segmentation of the outer contour, or the vascular surface of the blood vessel.

In addition, both steps S11 and S12 can optionally include the segmentation of further anatomical structures such as specific landmarks or the like in order to facilitate subsequent superimposition of the images REF and DU. According to an embodiment of the invention, template matching methods or an artificial neural network are used for segmentation of the reference image REF, but particularly for the current fluoroscopic image DU. This can greatly accelerate the segmentation, as a result of which the method is in principle suitable for quasi real time application.

A further step S13 entails superimposition or superposition of the reference image REF and the current fluoroscopic image DU. In other words, in step S13 the segmented structures corresponding to one another, in particular blood vessels, are superimposed on one another. A prerequisite for this is that the reference image REF has been registered relative to the coordinate system of the C-arm X-ray device. The result of step S13 is a superposition image SUP.

If no patient movements have occurred and there has been no deformation or displacement of the blood vessel due to the introduction of medical instruments into the blood vessel, the reference course and current course of the blood vessel in the superposition image SUP are substantially in conformity. The discrepancies are negligible. If there has been a patient movement and/or a displacement or deformation of the blood vessel due to the introduced medical instruments, the superposition image SUP flags up these discrepancies or differences in the courses of the vessels. To make the discrepancies even more evident to, for example, a surgeon, to whom the superposition image SUP is displayed, it is, for example, possible for the outer contours of blood vessels, location, orientation, center, shape and/or size of vascular branches in a blood vessel, stent landing zones, blood vessel circumferences or the like to be introduced, marked and/or highlighted in color.

A further step S14 entails a determination of at least one parameter characterizing a measure of discrepancy PAR ABW between the courses of the vessels. In this step, the discrepancy between the courses of the vessels is quantized. Possible parameters characterizing a measure of discrepancy PAR ABW can, for example, be: a distance between an outer contour of the blood vessel according to the reference course and the current course, a part of a blood vessel surface according to the current course, which, in the superposition image SUP, is outside the blood vessel surface according to the reference course, or the like.

Further embodiments of the parameter characterizing a measure of discrepancy are also conceivable. Alternatively or additionally, in step S14 it is also possible to determine as the parameter PAR ABW whether the medical instruments introduced into the blood vessel and segmented according to the current fluoroscopic image DU are inside or outside the blood vessel surfaces according to the reference image REF. In a last step S15 of this example embodiment of the method according to the invention, the previously determined measure of discrepancy ABW is displayed to the surgeon. To this end, the totality of all determined parameters characterizing the measure of discrepancy PAR ABW is taken into account and converted into an intuitive representation suitable for the surgical personnel.

For example, the measure of discrepancy ABW can be output by way of a traffic light display superimposed on the superposition image SUP. If the measure of discrepancy is within a first tolerance range or below a first threshold value S1, the traffic light in the superposition image SUP is switched to 'green' to indicate to the surgical personnel in an easily understandable manner that the quality of the superimposition of the reference image REF and the current fluoroscopic image DU is good. If the determined measure of discrepancy is within a second tolerance range or below a second threshold value S2 that is higher than the first tolerance range or the first threshold value S1, the traffic light in the superposition image SUP is switched to 'yellow' thus indicating to the surgical personnel in an easily understandable manner that the quality of the superimposition of the reference image REF and current fluoroscopic image DU can be corrected.

Correction of the superposition image SUP in the context of an embodiment of the invention is described in more detail below with reference to FIG. 2. If the determined measure of discrepancy is also outside the second tolerance range or above the second threshold value S2, the traffic light in the superposition image SUP is switched to 'red', hence indicating to the surgical personnel in an easily understandable manner that the quality of the superimposition of the reference image REF and the current fluoroscopic image DU is unusable due to significant differences between the structures in the two images and that it may be necessary to acquire a new modified fluoroscopic image MODU.

This procedure according to an embodiment of the invention is described in more detail below reference to FIG. 3. As an alternative to the traffic light display, it is also possible for a legend including a list of the determined values for all parameters characterizing the measure of discrepancy PAR ABW to be displayed in the superposition image SUP. Alternative solutions for displaying the measure of discrepancy ABW are also conceivable. Optionally, it can be provided according to the invention that steps S12 to S15 are repeated and to be precise for a plurality, preferably all of the fluorescent images DUi acquired continuously during the course of a medical intervention.

Insofar, in the i-th repeat loop (dashed arrow), the method according to an embodiment of the invention is applied to the i-th fluoroscopic image DUi. In particular in the variant, in which the measure of discrepancy is determined and displayed for all successive fluorescent images, it is advantageous to compare the same in the context of step S14 with that for the previous fluoroscopic image DUi-1 and thus check it for plausibility. This takes place under the assumption that changes in the course of the blood vessel between two consecutive fluorescent images DUi-1 and DUi are rather small.

Figure 3:
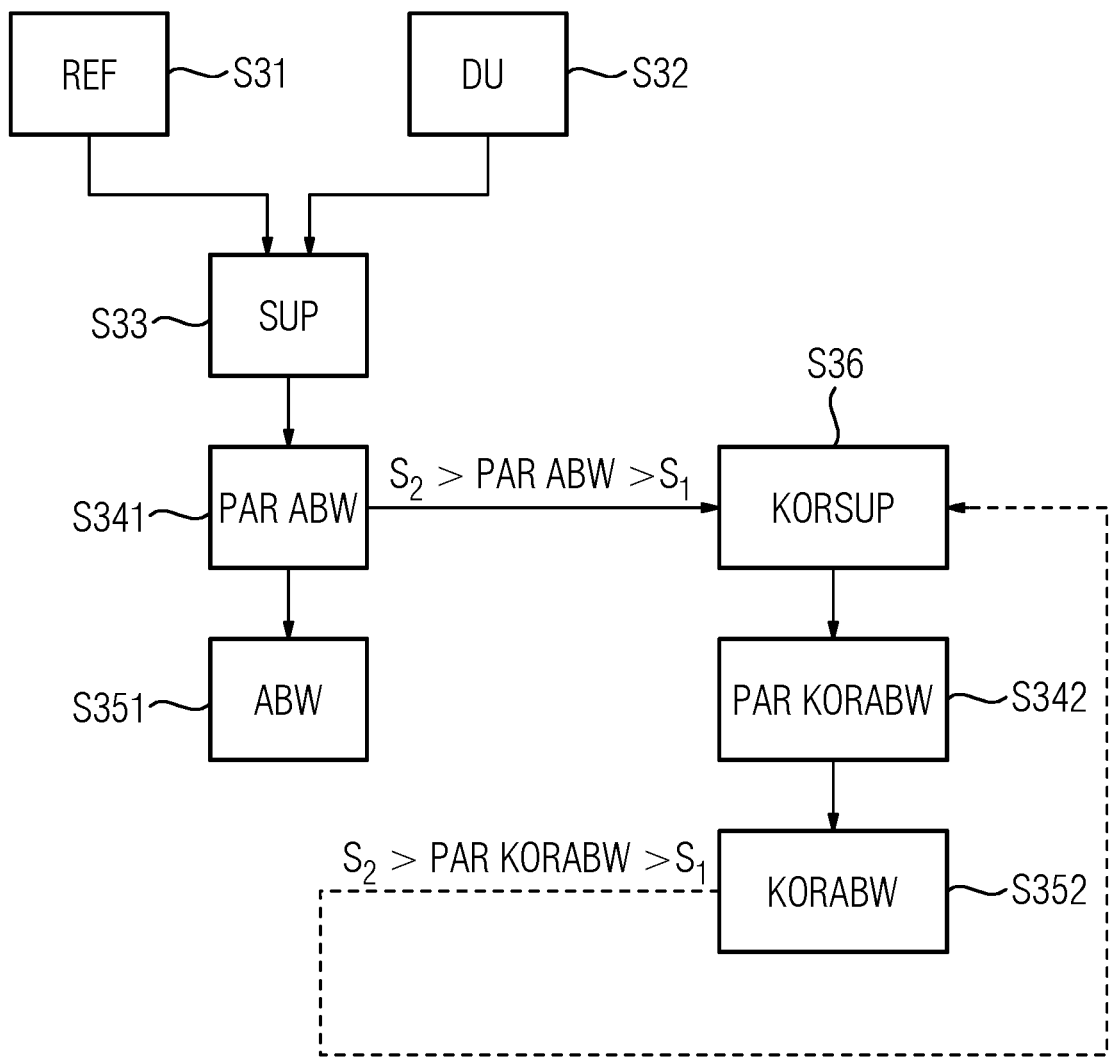

FIG. 3 is a schematic representation of a method according to the invention according to a further example embodiment of the present invention. Here, the object under observation is once again embodied as a blood vessel. Steps S31, S32, S33, S34 and S35 substantially correspond to steps S11 to S15 in FIG. 1. In this example embodiment step S341, the determination of at least one parameter for a measure of discrepancy PAR ABW, reveals that the measure of discrepancy ABW or at least one of the determined parameters PAR ABW is greater than a first threshold value S1 (and smaller than a second threshold value S2).

In this embodiment, according to step S36, at least one corrected superposition image KORSUP is generated automatically based on the at least one parameter characterizing a measure of discrepancy PAR ABW. In other words, for the discrepancy between the reference image REF and the current fluoroscopic image DU described by the value determined for this parameter PAR ABW, an operation is determined and is applied to align the determined reference course of the blood vessel to the current course of the blood vessel. The operation can be displacement, extension, compression, twisting, transposition and/or the like of the blood vessel or of part or section thereof. The result of step S36 is a corrected superposition image KORSUP.

Alternatively, the correction of the reference course of the blood vessel can be started or monitored by surgical personnel. For example, it can be provided that the user selects a suitable operation from a list of possible operations, or inputs a desired operation. For the corrected superposition image KORSUP, in step S342 at least one parameter characterizing a measure of discrepancy PAR KORABW is determined similarly to step S341. In step S352, the determined corrected measure of discrepancy KORABW is displayed to surgical personnel preferably together with the corrected superposition image KORSUP. If another check reveals that the corrected measure of discrepancy KORABW or at least one parameter characterizing a modified measure of discrepancy PAR KORABW is still above the first predetermined threshold value S1, in the context of a repeat loop with steps S36 to S352 (dashed arrow), further modified superposition images KORSUP can be generated and checked with respect to the quality of the superimposition until the first threshold value S1 is undershot. The repeat loop can also be cancelled by the user if the quality of the superimposition of the displayed corrected superposition image KORSUP is sufficient.

Figure 2:
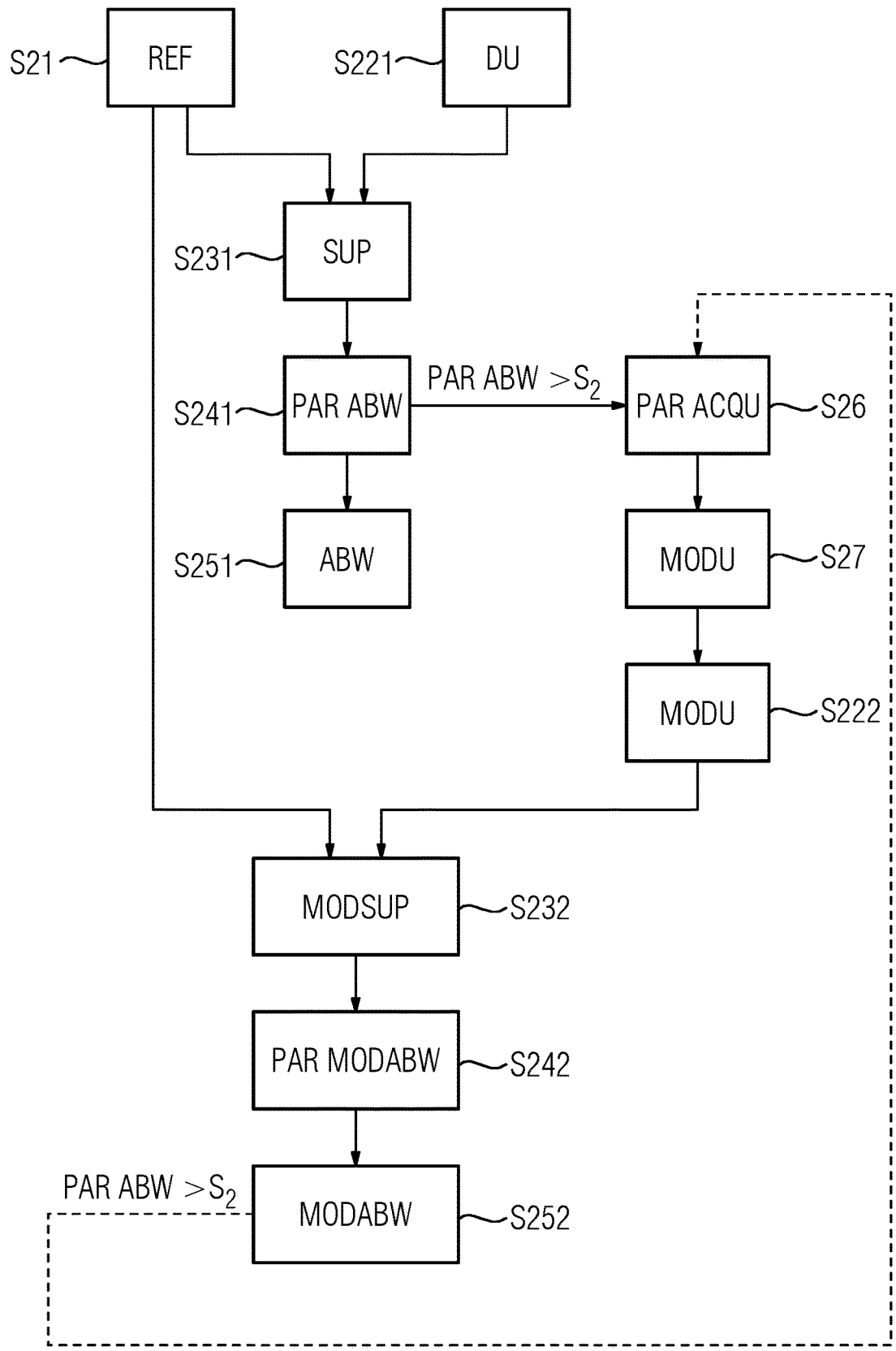

FIG. 2 is a schematic representation of a method according to the invention according to another example embodiment of the present invention. Here too, the object under examination is embodied as a blood vessel. Steps S21, S221, S231, S241 and S251 substantially correspond to steps S11 to S15 in FIG. 1. In this example embodiment step S241, the determination of at least one parameter for a measure of discrepancy PAR ABW, reveals that the measure of discrepancy ABW or at least one of the determined parameters PAR ABW is greater than the second threshold value S2.

In this embodiment, according to step S26, at least one acquisition parameter PAR ACQU is determined automatically for the medical imaging system. The acquisition parameter PAR ACQU is in particular changed angulation, changed collimation and/or changed X-ray voltage.

According to step S27, the changed acquisition parameter PAR ACQU can be used to acquire a modified fluoroscopic image MODU with a changed direction of view, a changed field of view or a changed contrast compared to the current fluoroscopic image. The image acquisition can take place automatically or by user confirmation of a suggested new acquisition. The determined acquisition parameter PAR ACQU can also be adapted by surgical personnel. The objective of this procedure is to provide a fluoroscopic image MODU, which, superimposed with the reference image REF, is more suitable than the current fluoroscopic image DU for a correction as described or with which a correction can be completely avoided. Similarly to step S221 or S12, in step S222, the modified fluoroscopic image MODU is also subjected to segmentation and then, in step S232, superimposed with the reference image REF for the generation of a modified superposition image MODSUP.

In steps S242 and S252, similarly to steps S241 and S251, at least one parameter characterizing a modified measure of discrepancy PAR MODABW is determined and the determined modified measure of discrepancy MODABW displayed for the surgical personnel, but here only relative to the modified superposition image MODSUP. If a repeat check reveals that the modified measure of discrepancy MODABW or at least one parameter characterizing a modified measure of discrepancy PAR MODABW is still above the second predetermined threshold value S2, in a repeat loop with steps S26 to S252 (dashed arrow), further changed acquisition parameters PAR ACQU for acquiring further modified fluorescent images MODU can be derived until the second threshold value S2 is undershot. The repeat loop can also be cancelled by the user if the quality of the superimposition of the displayed modified superposition image MODSUP is sufficient.

Figure 4:
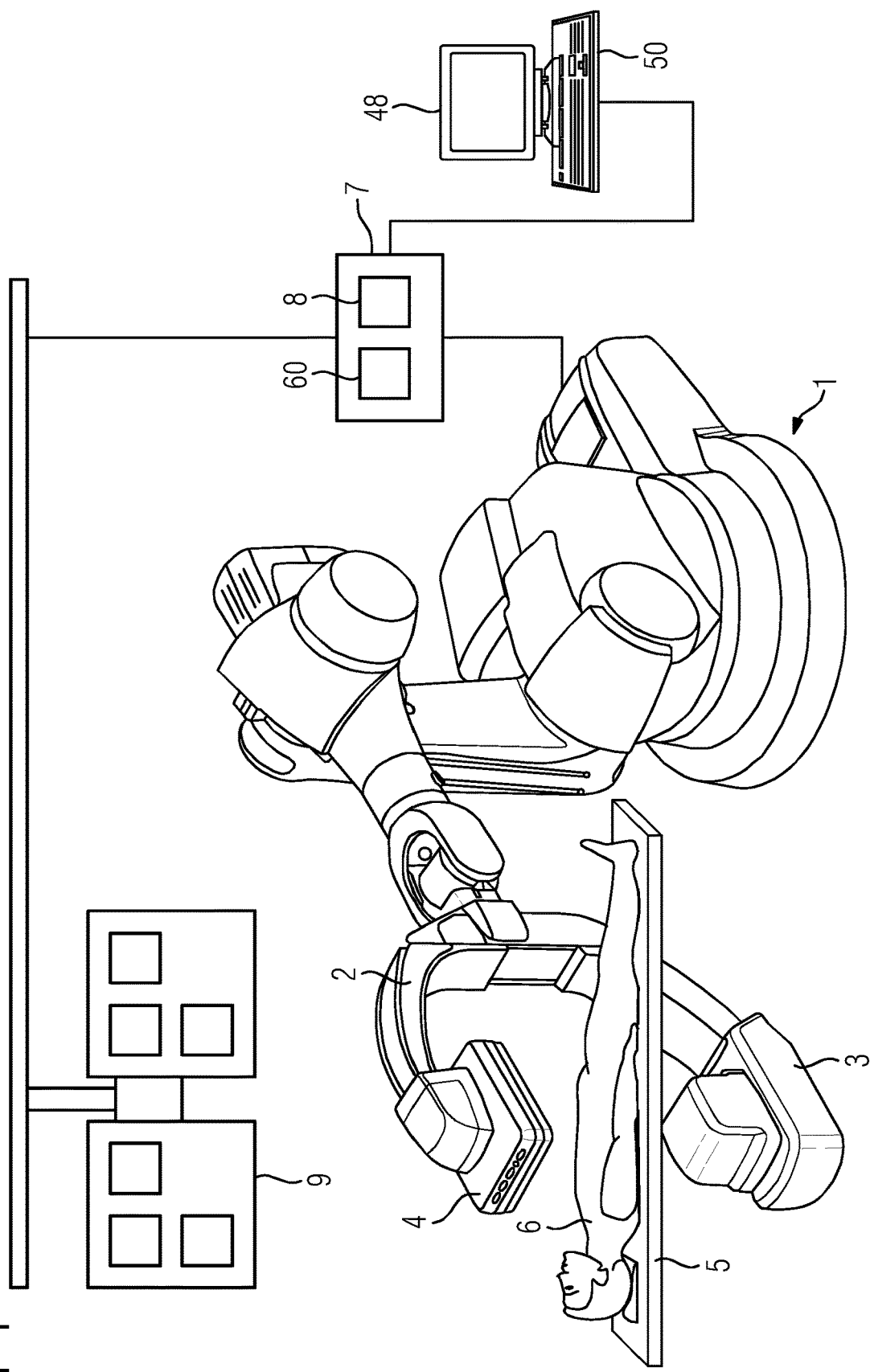

FIG. 4 shows a medical imaging system according to the invention 1 in an example embodiment. This is a monoplane angiographic X-ray system 1 in the form of a C-arm X-ray system with a C-arm 2 held by a stand in the form of a six-axis buckling arm robot, to the ends of which are attached an X-ray source, for example an X-ray emitter 3 with an X-ray tube and collimator, and an X-ray image detector 4.

The angiographic X-ray system 1 according to an embodiment of the invention can in particular be rotated about centers of rotation and axes of rotation in the C-arm plane of the X-ray image detector 4. Instead of the stand, the angiographic X-ray system can also comprise a normal ceiling-mounted or floor-mounted holder for the C-arm 2 or be embodied as mobile. The examination object is a patient 6 to be examined on a patient bench 5 located in the beam path of the X-ray emitter 3.

In this embodiment, the medical imaging system 1 includes a computing unit 7 in the form of a computer. The computing unit 7 is in principle embodied to receive and process the image signals acquired via the X-ray image detector 4, for example the current or modified fluoroscopic image DU, MODU. The processed X-ray images, for example (corrected/modified) superposition image SUP, KORSUP, MODSUP, can then be observed as a display on a traffic light monitor 9. The computing unit 7 can alternatively be designed as a standalone computing unit. The computing unit 7 is also in data communication with an output unit 48 and an input unit 50.

The output unit 48 is, for example, used for the graphical display of selection options for derived acquisition parameters PAR ACQU or correction operations to surgical personnel. The input unit 50 is used, for example, for the selection and/or confirmation of derived acquisition parameters PAR ACQU or correction operations by the surgical personnel. The output unit 48 can, for example, be an LCD, plasma or OLED screen. It can also be a touch-sensitive screen, which is also embodied as an input unit 50. The input unit 50 is, for example, a keyboard, a mouse, a so-called "touch screen" or even a microphone for voice input. The input unit 50 can also be configured to recognize a user's movements and convert them into corresponding commands.

The computing unit 7 is also connected to the X-ray image detector 4 and the X-ray emitter 3 for data exchange. For example, this can be control signals relating to derived acquisition parameters PAR ACQU with which a modified fluoroscopic image MODU is to be acquired. The data connections are in each case implemented in a known manner by wired or wireless device(s).

The computing unit 7 includes an image processing unit 8, which is configured to analyze X-ray images, in particular reference images REF and/or fluorescent images DU, MODU and to segment contained structures such as, for example, blood vessels and/or medical instruments. The image processing unit 8 is further configured to generate superposition images SUP, KORSUP, MODSUP by suitable registration of reference images REF and fluorescent images DU, MODU. The image processing unit 8 is further embodied to determine parameters characterizing a measure of discrepancy PAR ABW, PAR KORABW, PAR MODABW from a superposition image SUP, KORSUP, MODSUP and to derive therefrom correction operations for the generation of a corrected superposition image KORSUP and, if necessary, based on the determined parameters PAR ABW, to derive an acquisition parameter PAR ACQU.

To this end, the image processing unit 8 is also configured to compare a parameter characterizing a measure of discrepancy PAR ABW with predetermined threshold values S1, S2 or tolerance ranges. The threshold values S1, S2 can, for example, be stored in a memory 60 also comprised by the computing unit 7 for automatic retrieval. It can, in particular, depend upon the medical intervention performed or the body region of interest and also be individually adapted by surgical personnel.

The computing unit 7 can interact with a computer-readable data carrier, in particular to carry out a method according to an embodiment of the invention by a computer program with program code. The computer program can furthermore be stored retrievably on the machine-readable carrier. The machine-readable carrier can in particular be a CD, DVD, Blu-ray disk, memory stick or hard disk. The computing unit 7 can be embodied in the form of hardware or in the form of software. For example, the computing unit 7 is embodied as a so-called FPGA ("field programmable gate array") or includes an arithmetic logic unit.

In the example shown here, at least one computer program is stored in a memory 60 of the control unit 7 in order to carry out all the method steps of the method according to an embodiment of the invention when the computer program is executed on the computer. The computer program for carrying out the method steps of the method according to an embodiment of the invention includes program code. The computer program can also be embodied as an executable file and/or on another computing system. For example, the medical imaging system can be embodied such that the computing unit 7 loads the computer program for carrying out the method according to an embodiment of the invention into its internal working memory via an intranet or via the internet.

Figure 5:
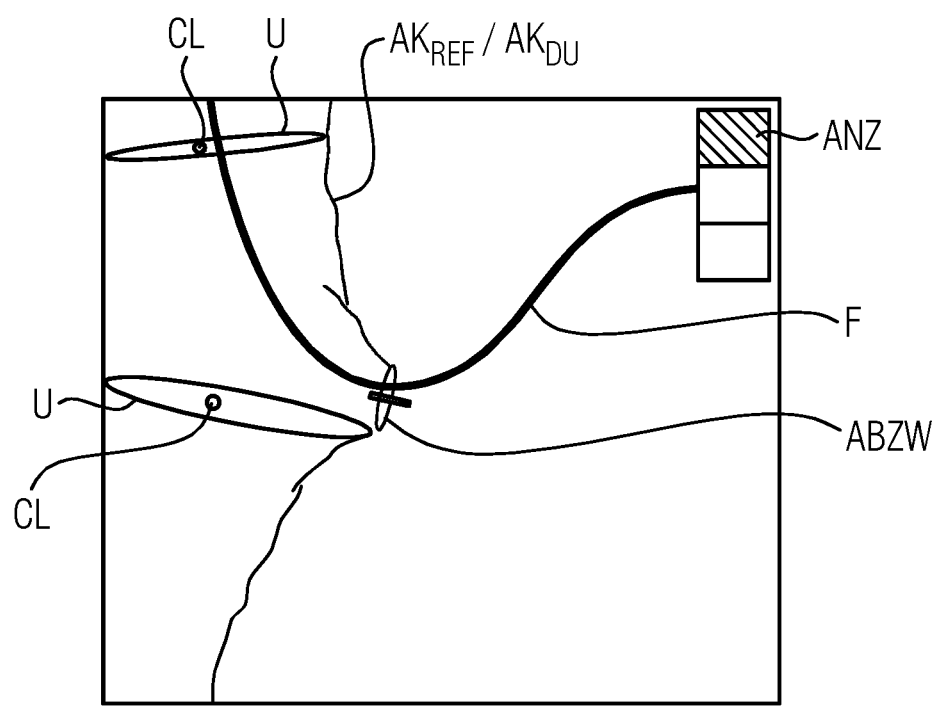
Figure 6:
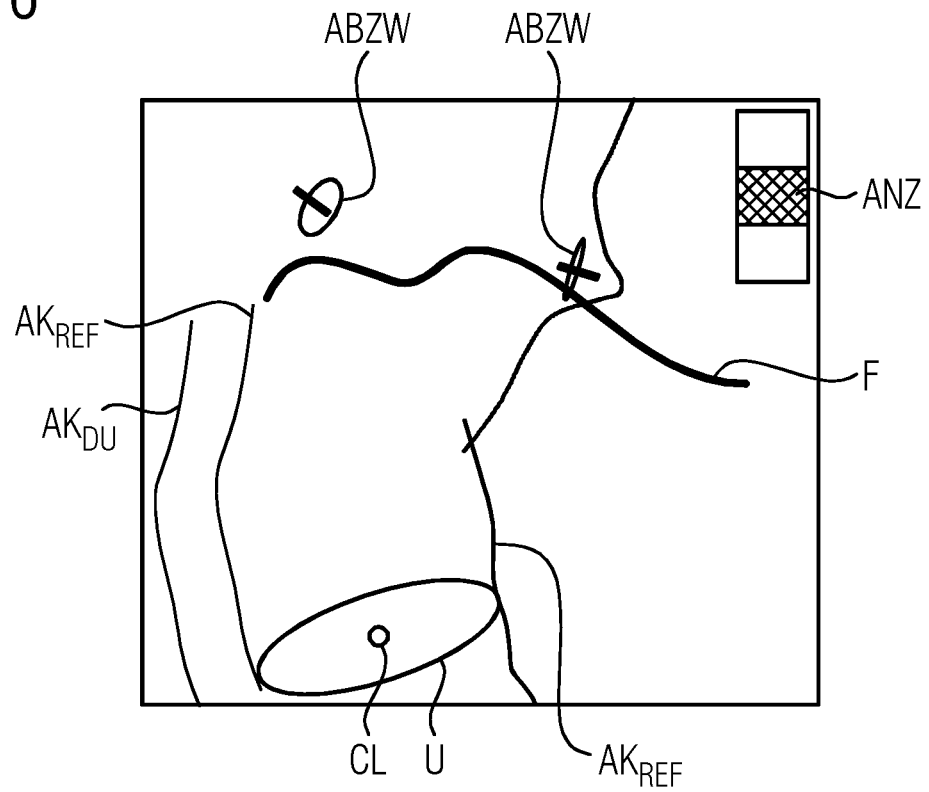

FIG. 5 and FIG. 6 each shown a superposition image SUP according to an example embodiment of the present invention. Here, once again, the object under observation is a blood vessel. In each case it is possible to identify segmented centerlines CL of a blood vessel, elliptically approximated blood vessel circumferences U, outer contours AKREF of the blood vessel according to the reference image REF and outer contours AKDU/AKMODU according to the fluoroscopic image DU/MODU, various guide wires F, elliptic approximated branch-off vessels/branches ABZW (and the centerlines thereof) and much more. In particular, it is also possible to identify the location of an already introduced stent graft in the blood vessel (compressed wave lines=wire mesh of the stent graft).

In FIG. 5, the guide wire F substantially extends centrally through the vessel branch ABZW. The outer vascular contours AKREF and AKDU also extend substantially in congruence. Overall, the measure of discrepancy is within a first acceptable tolerance range. It takes place as the superimposition of a display ANZ in the form of a traffic light on the superposition image, here set to 'green' (upper hatched box). No further correction steps are required. The superposition image shown in FIG. 5 can be a 'simple', corrected or modified superposition image SUP, MODSUP, KORSUP. In FIG. 6, the guide wire F extends with a clear offset to the centerline of the vascular branch ABZW.

Furthermore, the outer vessel contours AKREF and AKDU extend with a clear offset to one another. Overall, the measure of discrepancy is outside the first, but still inside a second, tolerance range. In other words, the superimposition can still be used if a correction method is used. The superposition image is superimposed with a display ANZ in the form of a traffic light, which is here set to 'yellow' (middle hatched box). Correction steps are required. These can be carried out automatically or semi-automatically as described above.

In a further case (not depicted), the determined discrepancies in the superposition image are outside the second tolerance range. In this case, the superposition image is superimposed with a display ANZ in the form of a traffic light, which is here set to 'red' (lower hatched box). As described above, the acquisition of a new, modified fluoroscopic image may be advisable.

Even if not explicitly described, but when advisable and within the meaning of the invention, individual example embodiments, individual partial aspects thereof or features can be combined with another or exchanged without departing from the scope of the present invention. Where applicable, advantages of the invention described with reference to one example embodiment also apply to other example embodiments, without this being explicitly mentioned.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for automatically checking a superposition image of a body region of interest of an examination object, the method comprising:
   determining at least one reference position of an object in a reference image;
   determining a current position of the object in a current fluoroscopic image;
   generating the superposition image by superimposing the current fluoroscopic image and the reference image;
   determining at least one parameter characterizing a measure of discrepancy between the at least one reference position of an object and the current position of the object in the superposition image; and
   displaying the measure of discrepancy determined, wherein the determining of the current position, the generating of the superposition image, the determining of the at least one parameter, and the displaying are performed in quasi real time.

2. The method of claim 1, wherein the determining of the current position of the object includes segmenting at least one of an instrument located in a blood vessel, an endoprosthesis, an outer contour and a volume of the object.

3. The method of claim 2, wherein the segmenting is performed using a neural network or by way of a template-matching technique.

4. The method of claim 2, wherein the determining of the current position, the generating of the superposition image; the determining of the at least one parameter, and the displaying are performed continuously for a plurality of successive fluorescent images.

5. The method of claim 4, wherein the determining of the at least one parameter characterizing the measure of discrepancy takes account of previous knowledge of segmented structures from at least one previously analyzed fluoroscopic image of the plurality of successive fluorescent images.

6. The method of claim 2, further comprising:
deriving, based on the at least one parameter characterizing the measure of discrepancy, at least one acquisition parameter for a medical imaging system, upon the at least one parameter determined, exceeding a threshold value for the measure of discrepancy;
acquiring a modified fluoroscopic image using the at least one acquisition parameter derived;
determining a current position of the object in the modified fluoroscopic image acquired;
generating a modified superposition image by superimposing the modified fluoroscopic image and the reference image;
determining at least one parameter characterizing a modified measure of discrepancy between the reference position and the current position of the object in the superposition image; and
displaying the modified measure of discrepancy.

7. The method of claim 2, further comprising:
automatically generating a corrected superposition image based on the at least one parameter characterizing the measure of discrepancy between the reference position and the current position of the object;
determining at least one parameter characterizing a corrected measure of discrepancy between the reference position and the current position of the object in the corrected superposition image automatically generated; and
displaying the corrected measure of discrepancy.

8. The method of claim 1, wherein the determining of the current position, the generating of the superposition image; the determining of the at least one parameter, and the displaying are performed continuously for a plurality of successive fluorescent images.

9. The method of claim 8, wherein the determining of the at least one parameter characterizing the measure of discrepancy takes account of previous knowledge of segmented structures from at least one previously analyzed fluoroscopic image of the plurality of successive fluorescent images.

10. The method of claim 1, further comprising:
deriving, based on the at least one parameter characterizing the measure of discrepancy, at least one acquisition parameter for a medical imaging system, upon the at least one parameter determined, exceeding a threshold value for the measure of discrepancy;
acquiring a modified fluoroscopic image using the at least one acquisition parameter derived;
determining a current position of the object in the modified fluoroscopic image acquired;
generating a modified superposition image by superimposing the modified fluoroscopic image and the reference image;
determining at least one parameter characterizing a modified measure of discrepancy between the reference position and the current position of the object in the superposition image; and
displaying the modified measure of discrepancy.

11. The method of claim 10, further comprising:
automatically generating a corrected superposition image based on the at least one parameter characterizing the measure of discrepancy between the reference position and the current position of the object;
determining at least one parameter characterizing a corrected measure of discrepancy between the reference position and the current position of the object in the corrected superposition image automatically generated; and
displaying the corrected measure of discrepancy.

12. The method of claim 1, further comprising:
automatically generating a corrected superposition image based on the at least one parameter characterizing the measure of discrepancy between the reference position and the current position of the object;
determining at least one parameter characterizing a corrected measure of discrepancy between the reference position and the current position of the object in the corrected superposition image automatically generated; and
displaying the corrected measure of discrepancy.

13. A non-transitory computer-readable data carrier, storing program code of a computer program, to carry out the method of claim 1 when the computer program is executed on a computer.

14. A computing unit for automatically checking a superposition image of a body region of interest of an examination object, comprising:
at least one processor, configured to:
determine at least one reference position of an object in a reference image;
determine a current position of the object in a current fluoroscopic image;
generate the superposition image by superimposing the current fluoroscopic image and the reference image;
determine at least one parameter characterizing a measure of discrepancy between the at least one reference position of an object and the current position of the object in the superposition image; and
display the measure of discrepancy determined wherein the at least one processor is configured to determine the current position, generate the superposition image, determine the at least one parameter, and display the measure of discrepancy in quasi real time.

15. The computing unit of claim 14, connected to a medical imaging system, wherein control signals, relating to corrected at least one acquisition parameter or current fluorescent image, are transmittable between the medical imaging system and the computing unit.

16. A medical imaging system comprising the computing unit of claim 14.

17. The computing unit of claim 14, wherein the at least one processor is configured to determine the current position of the object by being configured to segment at least one of an instrument located in a blood vessel, an endoprosthesis, an outer contour and a volume of the object.

18. The computing unit of claim 17, wherein the at least one processor is configured to segment using a neural network or by way of a template-matching technique.

19. A method for automatically checking a superposition image of a body region of interest of an examination object, the method comprising:
- determining at least one reference position of an object in a reference image;
- determining a current position of the object in a current fluoroscopic image;
- generating the superposition image by superimposing the current fluoroscopic image and the reference image;
- determining at least one parameter characterizing a measure of discrepancy between the at least one reference position of an object and the current position of the object in the superposition image; and
- displaying the measure of discrepancy determined, wherein the determining of the current position of the object includes segmenting at least one of an instrument located in a blood vessel, an endoprosthesis, an outer contour and a volume of the object.

20. The method of claim 19, wherein the determining of the current position, the generating of the superposition image; the determining of the at least one parameter, and the displaying are performed continuously for a plurality of successive fluorescent images.

* * * * *